(12) United States Patent
Hsieh et al.

(10) Patent No.: US 9,034,397 B2
(45) Date of Patent: May 19, 2015

(54) METHOD FOR TREATING OBESITY

(71) Applicant: Tunghai University, Taichung (TW)

(72) Inventors: Chang-Chi Hsieh, Taichung (TW);
Chin-Tung Wu, Taichung (TW); Jie-Yu Chen, Taichung (TW); Yi-Chieh Li, Taichung (TW); Hsin-Sheng Tsay, Taichung (TW)

(73) Assignee: Tunghai University, Taichung (TW)

( * ) Notice: Subject to any disclaimer, the term of this patent is extended or adjusted under 35 U.S.C. 154(b) by 0 days.

(21) Appl. No.: 14/066,764

(22) Filed: Oct. 30, 2013

(65) Prior Publication Data

US 2014/0288186 A1    Sep. 25, 2014

(30) Foreign Application Priority Data

Mar. 19, 2013  (TW) .............................. 102109691 A (51) Int. Cl.
*A61K 36/00*    (2006.01)
*A61K 36/8984*    (2006.01)
*A61K 31/09*    (2006.01)

(52) U.S. Cl.
CPC ............. *A61K 36/8984* (2013.01); *A61K 31/09* (2013.01); *Y10S 514/909* (2013.01)

(58) Field of Classification Search
CPC ........................ A61K 31/105; A61K 36/8984
USPC ........................................... 424/725; 514/909
See application file for complete search history.

(56) References Cited

FOREIGN PATENT DOCUMENTS

KR    2013047458  A  *  5/2013

OTHER PUBLICATIONS

KR 2013047458A (2013) English Translation.*

* cited by examiner

*Primary Examiner* — Kevin E Weddington (57) ABSTRACT

The present invention provides methods of administering a *Dendrobium* polyphenol in an amount effective to lower blood sugar, treat hepatic disease, obesity or diabetes. Exemplary hepatic disease includes fibrosis, fatty liver and hepatitis. Moreover, the *Dendrobium* polyphenol is extracted from the plants of the genus *Dendrobium*.

3 Claims, 10 Drawing Sheets

METHOD FOR TREATING OBESITY

FIELD OF INVENTION

The present invention relates to a method for lowering blood glucose and method for treating and/or preventing disease including hepatic disease, obesity and diabetes.

BACKGROUND OF INVENTION

Recently, the altering life style in the modern society results in the switch of dietary habits from meals at home to eating out. The long-term eating out causes the unbalanced food intakes including decreased vegetables intake and increased meats intake. Despite the unbalanced nutrition intakes, the altered dietary habit also causes obesity and metabolic diseases resulted from the excessive oil, sugar and salt in the foods. Obesity not only affects the beautiful outside, but also results in some physiological abnormalities that lead to increased incidence of noninfectious diseases and elevated lethal rate. For example, fatty liver is caused by the accumulation of excessive hepatic lipid that abolishes the normal lipid metabolism in liver. The abnormal accumulation of excessive lipid in liver would further directly or indirectly lead to the occurrence of type II diabetes that severely damage the life quality of patients.

Furthermore, fatty liver is diagnosed while the weight of hepatic lipid is more than 10% of the total weight of liver. The patient with mild fatty liver exhibits no obverts damage to the health. However, the long-term fatty infiltration of the liver could cause chronic hepatic inflammation that increases the risk of hepatic diseases such as liver cirrhosis and hepatoma. In addition, the decreased synthesis of HDL (high density lipoprotein) and increased synthesis LDL (low density lipoprotein) and very low-density lipoprotein in the fatty liver patient would further result in hyperlipidemia that elevates the incidence of stroke and heart disease.

Diabetes is the one of the most common chronic disease and is usually ignored by the patients due to the mild symptom at early stage of the disease progression. However, the diabetes would cause many chronic complications including renal diseases, retinal disorder, elevated risk of arteriosclerosis and progressed cardiovascular diseases. Moreover, the statistic data show that there are approximately half of fatty liver patients combining with the occurrence of diabetes. In the other hand, almost half of diabetes patients are diagnosed with the fatty liver. The association of fatty liver and diabetes in the clinical is resulted from synthesis and accumulation of hepatic triacylglycerol that is induced by the hyperinsulinemia and insulin resistant in the obese diabetes patients. Currently, there is no applied drug for completely curing both diseases resulted from the lipid accumulation in liver. However, the appropriated pharmaceutical treatment with good living habits is the only way to control and prevent the progression of both diseases.

In order to improve the side effects resulted from the chemical drug on people who have the modern health concepts, the medical plants such as *Dendrobium* species are investigated for the applications in the recent years. The genus *Dendrobium* belongs to familia Orchidaceae and distributes in tropical and subtropical area. The members of genus *Dendrobium* are usually applied to the uses as cut flowers and potted orchids for ornament. Including 15 species distributing in Taiwan, there are 1600 species in the genus *Dendrobium* in the worldwide. Either dry or fresh stem of genus *Dendrobium* is a precious Chinese herb named as *Dendrobium* spp. (Herba Dendrobii) that is widely used in traditional chinese-medicine to bring down a fever, cure the ophthalmology diseases or other nourishing purpose. According to the recent studies, the genus *Dendrobium* contains many bioactive substances such as phenanthrenes, bibenzyls, fluorenones, sesquiterpenes and alkaloids. These substances exhibit different bio-activities such as anti-inflammatory, anti-oxidant and anti-allergic activities.

Collectively the genus *Dendrobium* is a healthy and precious pharmaceutical plant. However, the application of genus *Dendrobium* in the management of hepatic diseases and diabetes is never claimed. Therefore, the inventors of the invention participate in the investigations of the bioactive substances in the genus *Dendrobium* on improvement of the diabetes or hepatic diseases.

SUMMARY OF INVENTION

The present invention is based on the discovery that administrating a *Dendrobium* polyphenol to a subject is to regulate blood sugar, and treat or prevent disease including hepatic disease, obesity or diabetes. Accordingly, in a first aspect, the invention provides a method for lowering blood sugar, comprising administration of a therapeutically effective amount of *Dendrobium* polyphenol to a subject in need thereof, wherein the *Dendrobium* polyphenol is extracted from the plants of the genus *Dendrobium*, such as *Dendrobium tosaense*.

Furthermore, the *Dendrobium* polyphenol is a non-polysaccharides mixture at least including gigantol of formula (I):

In second aspect, the invention provides method for treating hepatic disease, such as fatty liver, liver cirrhosis, hepatic fibrosis and hepatitis, comprising administration of a therapeutically effective amount of *Dendrobium* polyphenol to a subject in need thereof, wherein the *Dendrobium* polyphenol is extracted from the plants of the genus *Dendrobium*, such as *Dendrobium tosaense*. Moreover, the *Dendrobium* polyphenol is a non-polysaccharides mixture at least including gigantol of formula (I).

In third aspect, the invention provides method for treating obesity comprising administration of a therapeutically effective amount of *Dendrobium* polyphenol to a subject in need thereof, wherein the *Dendrobium* polyphenol is extracted from the plants of the genus *Dendrobium*, such as *Dendrobium tosaense*. Moreover, the *Dendrobium* polyphenol is a non-polysaccharides mixture at least including gigantol of formula (I).

In forth aspect, the invention provides method for treating diabetes comprising administration of a therapeutically effective amount of polyphenol to a subject in need thereof, wherein the *Dendrobium* polyphenol is extracted from the plants of the genus *Dendrobium*, such as *Dendrobium tosaense*. Moreover, the *Dendrobium* polyphenol is a non-polysaccharides mixture at least including gigantol of formula (I).

BRIEF DESCRIPTION OF THE DRAWINGS

FIG. 7 shows the results obtained by histologically analyzing hepatic histology by H&E staining, wherein FIG. 7A shows group 1, FIG. 7B shows group 2, FIG. 7C shows group 3 and FIG. 7D shows group 4.

FIG. 12 shows the results obtained by histologically analyzing hepatic histology by H&E staining, wherein FIG. 12A shows group 1, FIG. 12B shows group 2, FIG. 12C shows group 3 and FIG. 12D shows group 4.

FIG. 13 shows the results obtained by histologically analyzing hepatic histology by sirius red staining, wherein FIG. 13A shows group 1, FIG. 13B shows group 2, FIG. 13C shows group 3 and FIG. 13D shows group 4.

DETAILED DESCRIPTION OF THE INVENTION

In the following context, the examples and figures are used for illustrating the detail of this invention. The invention discloses a *Dendrobium* polyphenol that is a non-polysaccharides mixture extracted from *Dendrobium*. Furthermore, in the following detailed description of the invention using *Dendrobium tosaense* for extracting the *Dendrobium* polyphenol is merely exemplary and is not to limit the invention to the forms disclosed.

Example 1

Preparation of the *Dendrobium* Polyphenol

Figure 1:
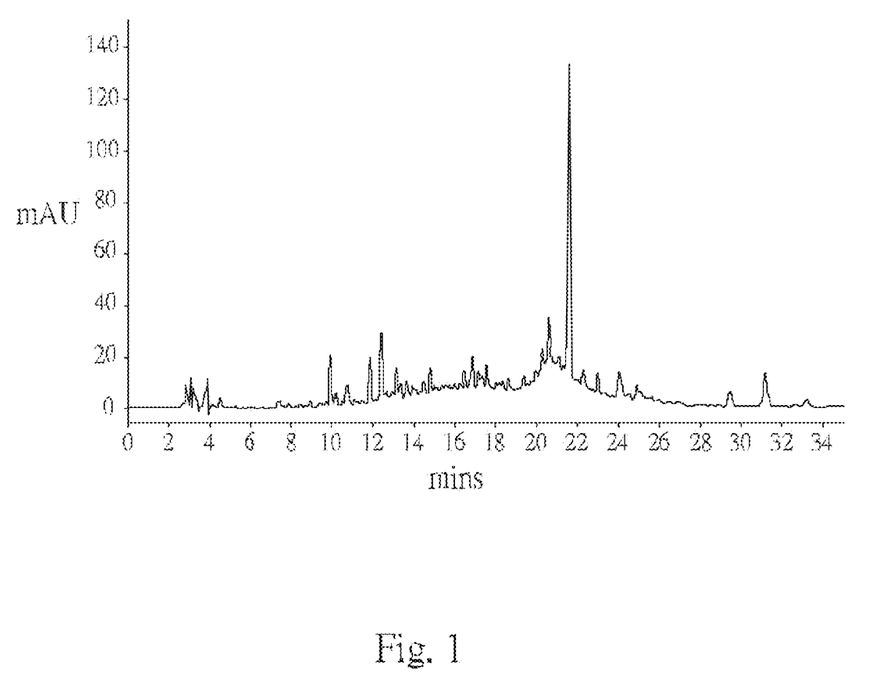
FIG. 1 shows an HPLC chromatogram of *Dendrobium* polyphenol.

First, a dehydrated stem of *Dendrobium tosaense* was ground into powder. Dissolving 30 gram of powder ground from the stem of dry *Dendrobium tosaense* with 300 uL methanol and that was followed by sonication for 10 minutes to obtain the *Dendrobium*/methanol mixture. Sequentially separating the methanol extracting substances by n-hexane for three times, ethyl acetate (EA) for three times and chloroform for three times. Finally, a *Dendrobium* polyphenol was extracted by removing the filtrate. Moreover, the extracted *Dendrobium* polyphenol was further analyzed by high performance liquid chromatography (HPLC) and is shown in FIG. 1.

Example 2

The *Dendrobium* Polyphenol Containing Gigantol

Figure 2:
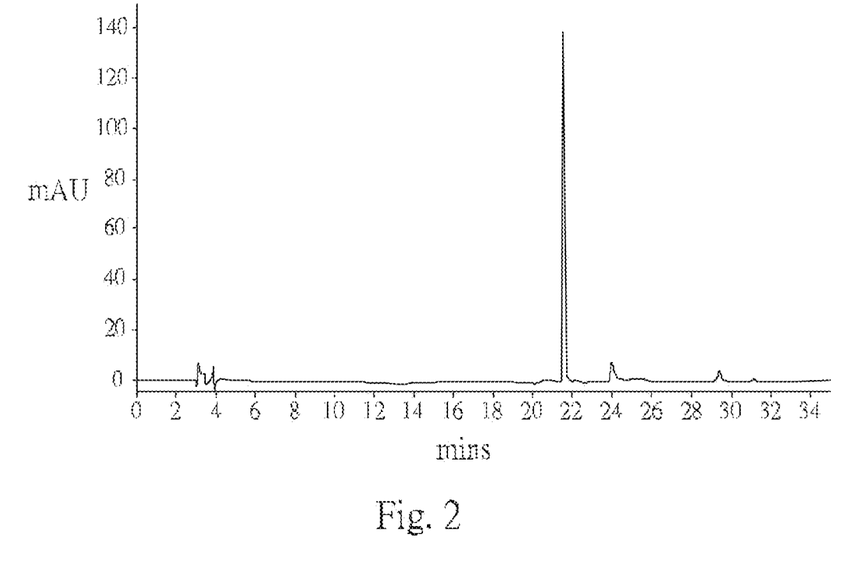
FIG. 2 shows an HPLC chromatogram of standard of gigantol.
Figure 3:
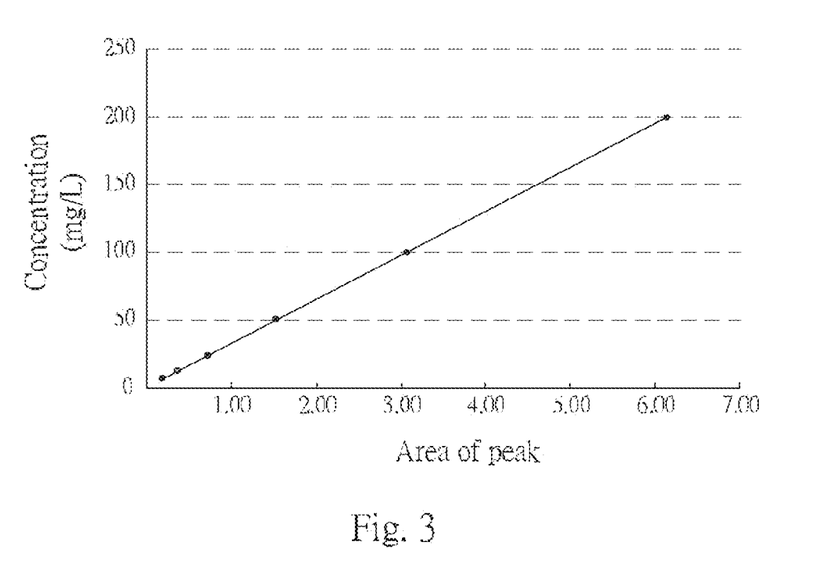
FIG. 3 shows a standard curve of gigantol.

The standard of gigantol was analyzed by HPLC analysis with a predetermined condition and the result is shown in FIG. 2. Moreover, analyzing gigantol with different concentration as 6.25 mg/L, 12.5 mg/L, 25 mg/L, 50 mg/L, 100 mg/L and 200 mg/L by HPLC to generate a linear regression line is shown in FIG. 3. The linear regression line of FIG. 3 represents a formula of $Y=32.363X-1.003 (R^2=0.9999)$.

The results in FIG. 2 shows that the retaining time of gigantol in the column is about 22 minute. The comparison of HPLC spectrums shown in FIG. 1 and FIG. 2 indicates that there is obvious peak with the retaining time about 22 minutes in the FIG. 1. It suggests that the *Dendrobium* polyphenol presenting in this invention at least includes gigantol. Furthermore, the amount of the gigantol in the *Dendrobium* polyphenol is $100.26\pm1.85$ μg/g determined by the formula of linear regression line.

Example 3

Preparation of Fatty Liver Mouse Model

The C57BL/6 wild type mice were divided into four groups that were accommodated the environment for one week and were followed by different administration protocol for 8 weeks. Herein, the group 1 was the control mice with normal feeding condition; the group 2 was fed with the drinking water that contains 30% fructose to induce fatter liver; the group 3 was fed with the drinking water that contains 30% fructose and the low dose of the *Dendrobium* polyphenol (10 mg/Kg) disclosed in this invention; the group 4 was fed with the drinking water that contains 30% fructose and the high dose of the *Dendrobium* polyphenol (50 g/Kg) disclosed in this invention.

Example 4

*Dendrobium* Polyphenol can Decrease Body Weight

Figure 4:
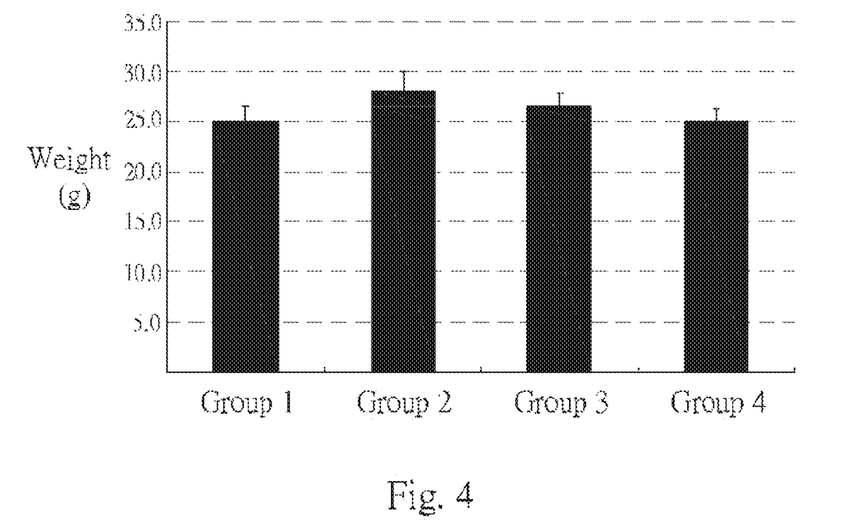
FIG. 4 shows body weights of each group of mice.

The body weights of the mice in each group indicated in example 3 were measured and shown in FIG. 4. The result shows that the body weight of the group 2 is significantly greater than in the group 1. It suggests that administration with fructose containing water leads to increased body weight and induces fatty liver. In contrast to the group 2, the body weight of the group 3 and the group 4 with accompanied administration with the *Dendrobium* polyphenol are significantly lower than that of the group 2. It suggests that administration of rge *Dendrobium* polyphenol regardless of high dose or low dose exhibits the efficacy in decreasing body weight.

Example 5

*Dendrobium* Polyphenol can Lower the Concentration of ALT in the Serum

Figure 5:
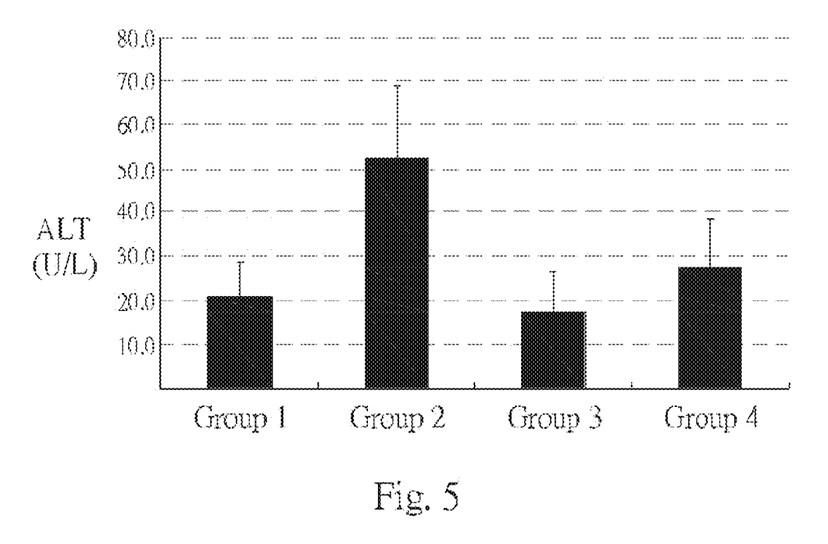
FIG. 5 shows the concentration of ALT (Alanine transaminase) in the serum of each group of mice.

Alanine Aminotransferase (ALT) is a hepatic enzyme that is applied as the indicator for examining the liver functions. The ALT concentration in the serum higher the normal value indicates the damages or inflammation occurred in liver. Therefore, the ALT concentrations in the serum collected from the mice in each group were detected for demonstrating the liver functions. The results shown in FIG. 5 reveals that the ALT concentration in the serum of the group 2 is significantly greater than that of the group 1. The result indicates that the administration of high concentration of fructose containing water elevates the ALT concentration in the serum that shall cause the damages in liver. With the comparison of the group 2, the ALT concentrations in the serum of the group 3 and the group 4 are significantly reduced. It suggests that the administration of either high does or low does of the *Dendrobium* polyphenol reveals the function in lowering the ALT concentration in the serum.

Example 6

*Dendrobium* Polyphenol can Suppress Fatty Liver Progression

Figure 6:
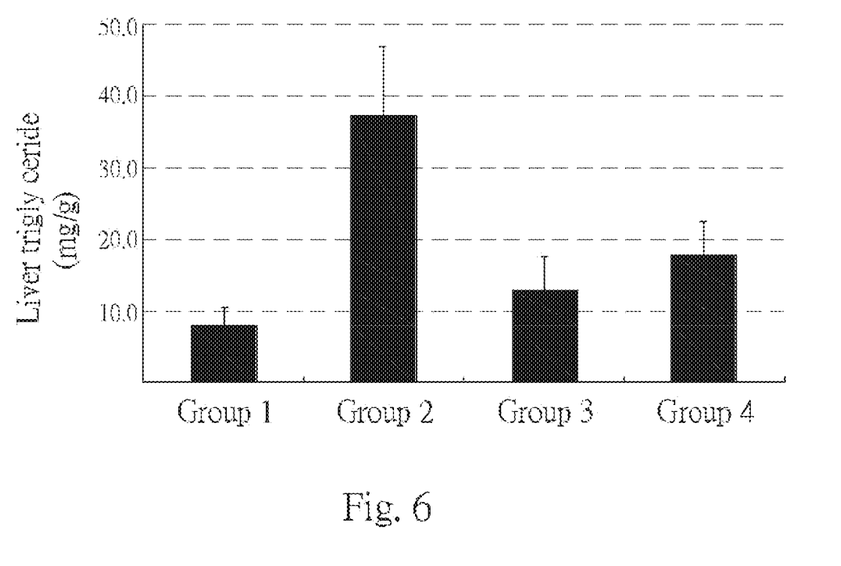
FIG. 6 shows the concentration of hepatic triglyceride of each group of mice.

The hepatic triglyceride content detected from the mice in each group established in example 3 are shown in FIG. 6. The result in FIG. 6 shows that the hepatic triglyceride content detected from the group 2 is significantly greater than that from the group 1. The difference of hepatic triglyceride contents between the group 2 and the group 1 suggests that the administration with high concentration of fructose containing water leads to fatty liver through accumulation of hepatic triglyceride. Compared to the hepatic triglyceride content of the group 2, the hepatic triglyceride content of either the group 3 or the group 4 reveals significantly decrease. Accordingly, it suggests that administration with either low dose or high dose of the *Dendrobium* polyphenol can efficiently decrease the synthesis of hepatic triglyceride in liver and suppress fatty liver formation.

Figure 7:
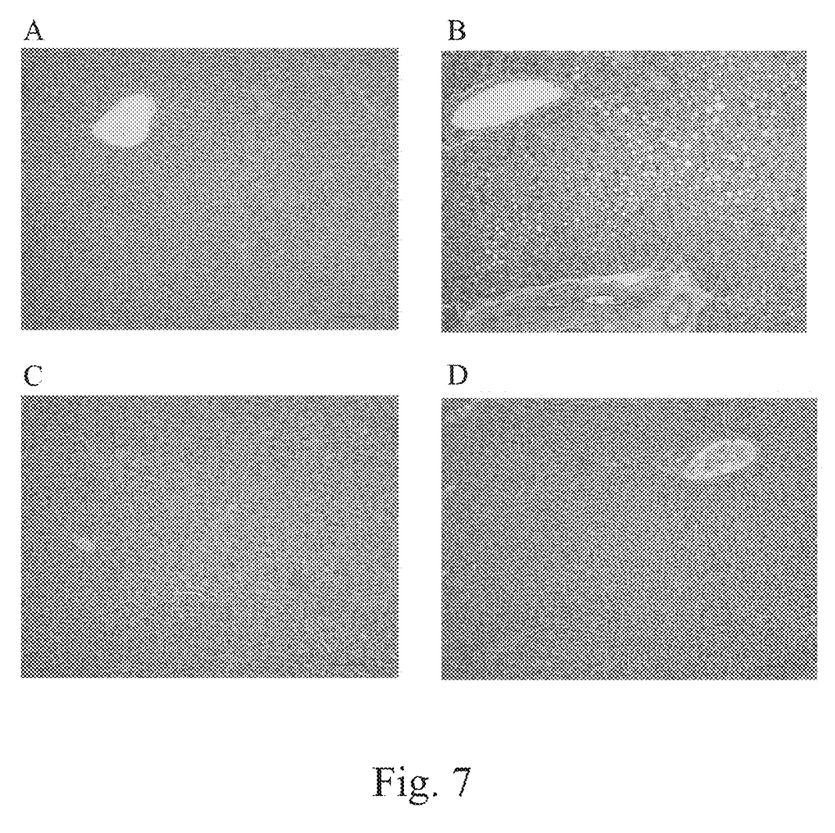

Moreover, the livers of the mice of the four groups were respectively fixed with formalin for the paraffin embedding and histological section. The histology of liver shown in FIG. 7 are present by microscopy after the processes including H&E staining, dehydration and mounting. Herein, FIG. 7A shows the hepatic histology of the group 1; FIG. 7B shows the hepatic histology of the group 2, FIG. 7C shows the hepatic histology of the group 3, FIG. 7D shows the hepatic histology of the group 4. The results in FIG. 7 suggest that the mice fed with high concentration of fructose containing water in the group 2 bear the fatty liver. The fatty liver mouse model exhibits excessive adipose tissue with obvious fat vacuoles in the liver. In contrast, the livers of the group 3 and the group 4 reveal less adipose tissue and fat vacuoles with comparison of the group 2. These results indicate the *Dendrobium* polyphenol can suppress the formation of fatty liver.

Example 7

*Dendrobium* Polyphenol can Regulate Blood Glucose

Figure 8:
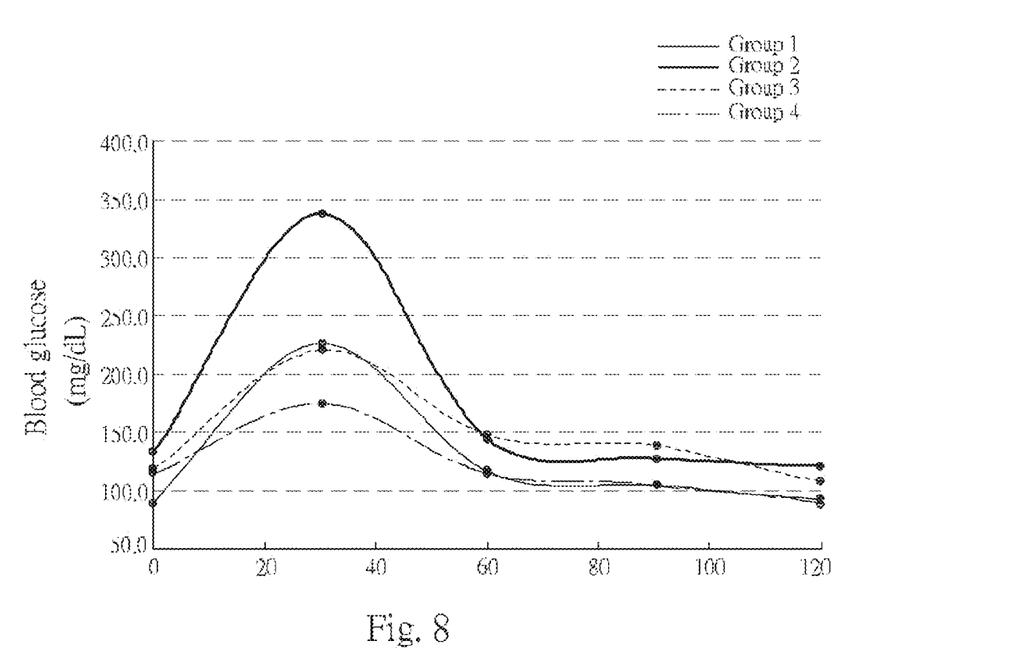
FIG. 8 shows the results of glucose tolerance test of each group of mice.

The insulin resistance is the leading cause of type II diabetes that the reduction of blood sugar is fail be stimulated by the specific concentration of insulin. The failure in lowering the blood sugar by insulin lead to the high concentration of glycemia in the most type II diabetes patients. In this example, the blood sugar levels of the mice in each group established in example 3 were measured before glucose treatments. After the measurement, all mice were orally fed with 2.0 g/kg glucose. The each group was respectively measured its blood sugar at 30, 60, 90 and 120 minutes after glucose administration. The results of the blood sugar of the mice in each group are shown in FIG. 8. In FIG. 8, the elevated blood sugar of the group 2 reveals the significant increase compared to the group 1. The significant increase of the blood sugar of the group 2 suggests that the administration of glucose on the mice is sufficient to induce the insulin resistance. Furthermore, the mice of the group 3 and the group 4 reveal lower concentration of blood sugar at 30, 60 and 120 minutes after glucose treatment with the comparison of the group 2. The significantly reduced blood sugar of the group 3 and group 4 suggests that either low dose or high dose of the *Dendrobium* polyphenol is sufficient to regulated the glycermia homeostasis and suppress the occurrence of insulin resistance.

Example 8

Preparation of Hepatitis Mouse Model

After one week of adaptation to environment, all the ICR mice divided in four groups were fed with different administration protocols for eight weeks. Herein, the group 1 was the control mice without any treatment; the group 2 was intraperitoneally injected with 200 mg/kg thioacetamide (TAA) to induce the hepatitis; the group 3 was intraperitoneally injected with 200 mg/kg TAA and 10 mg/kg *Dendrobium* polyphenol present in this invention; the group 4 was intraperitoneally injected with 200 mg/kg TAA and 50 mg/kg *Dendrobium* polyphenol present in this invention Example 9

*Dendrobium* Polyphenol can Suppress Hepatitis

Figure 9:
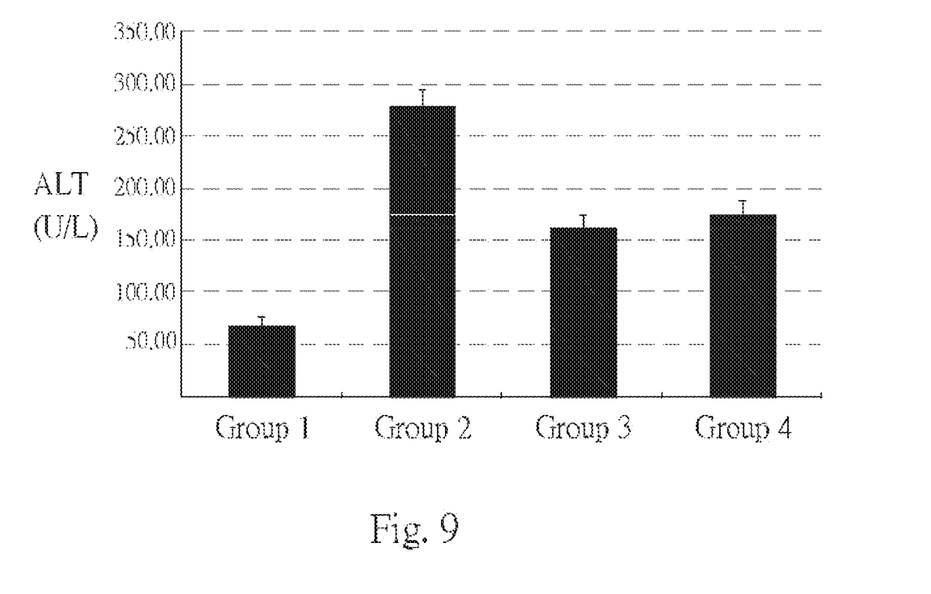
FIG. 9 shows the concentration of ALT (Alanine transaminase) in the serum of each group of mice.
Figure 10:
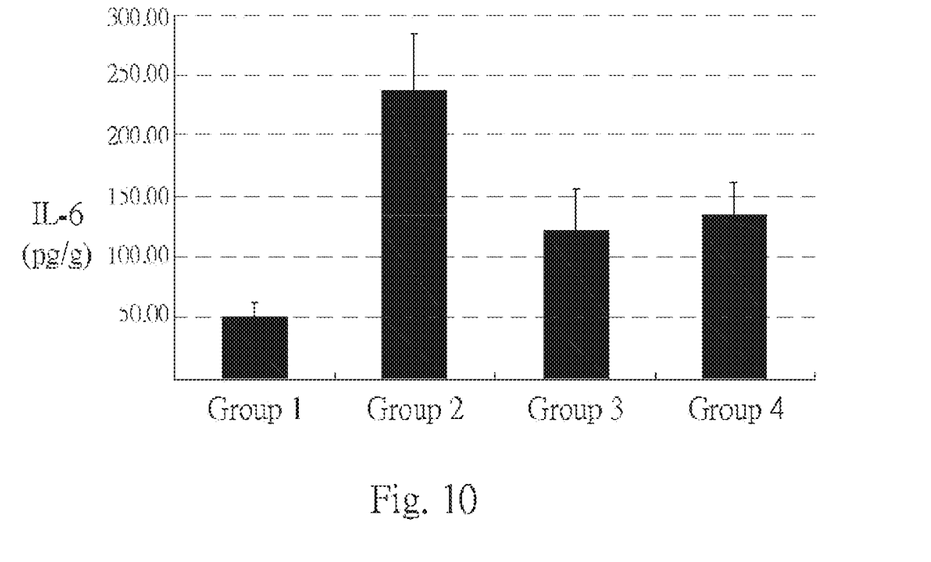
FIG. 10 shows the expression levels of IL-6 in the liver of the mice in each group.

The measured ALT in serum and IL-6 in liver of the mice in the four groups are showed in FIG. 9 and FIG. 10. Herein, FIG. 9 shows the ALT concentration in the serum of the each group and FIG. 10 reveals the IL-6 amount in the liver of the each group. In FIG. 9, the ALT in the serum of in the group 2 is significantly increased with comparison of the group 1. The increased ALT in the group 2 suggests that injection with TAA is sufficient to elevate the ALT concentration in the mouse serum. Furthermore, the ALT in the serum of the mice in the group 3 and the group 4 are significantly decreased with the comparison of the group 2.

In FIG. 10, the hepatic IL-6 of the group 2 is significantly higher than that of the group 1. This result suggests that the group 2 bear hepatitis after TAA injection. Furthermore, the hepatic IL-6 of the group 3 and group 4 are significantly decreased with the comparison of the group 2.

These results suggest that TAA injection on the mice would cause hepatitis that elevates the ALT level in the serum. Administration with either high or low dose of the *Dendrobium* polyphenol disclosed in this invention is sufficient to suppress the hepatitis in the mice.

Example 10

*Dendrobium* Polyphenol can Suppress to Form Fibrosis and Fatty Liver

Figure 11:
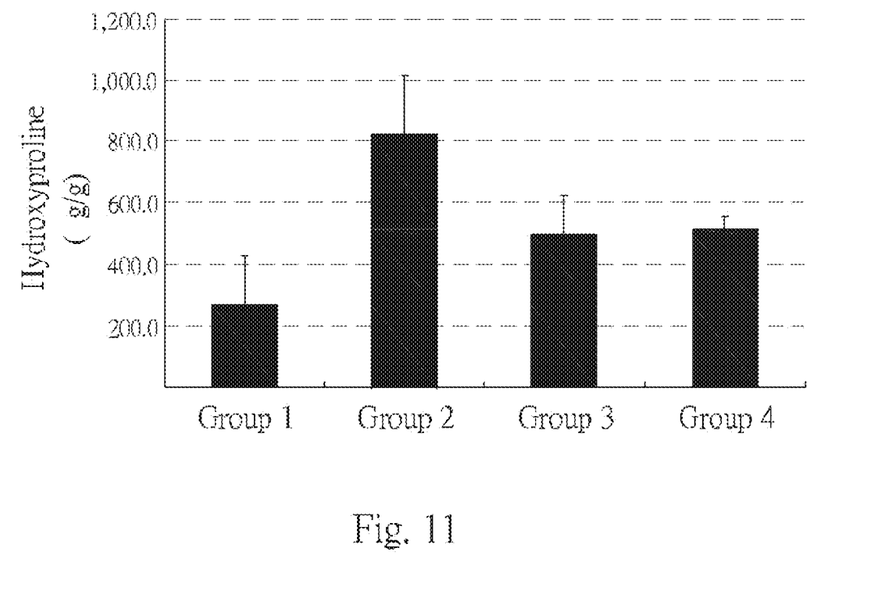
FIG. 11 shows the measurements of liver hydroxyproline content of each group of mice.
Figure 12:
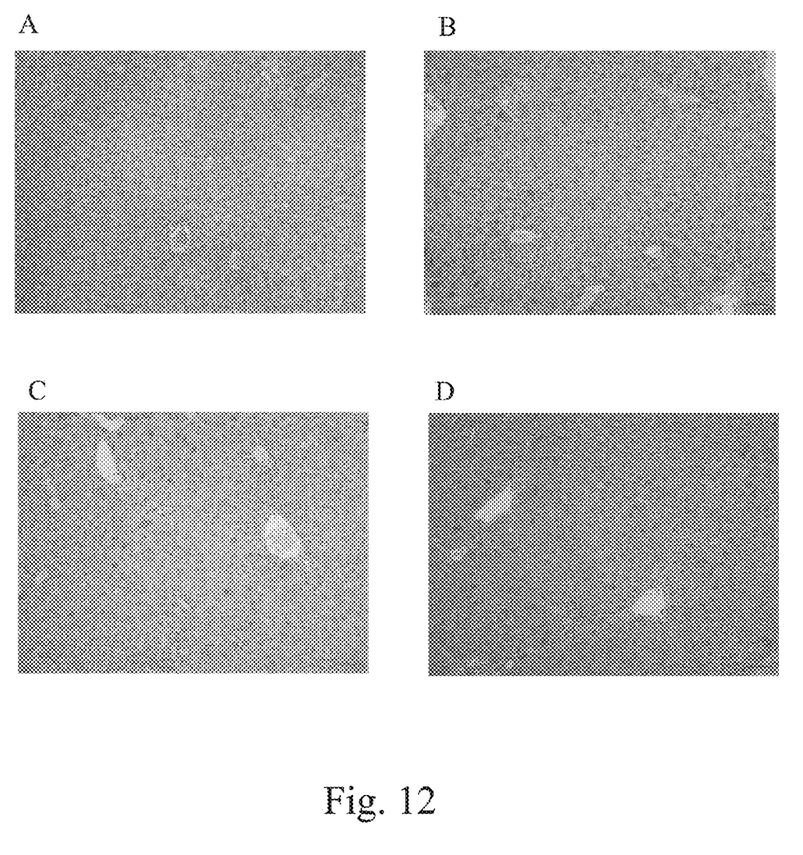
Figure 13:
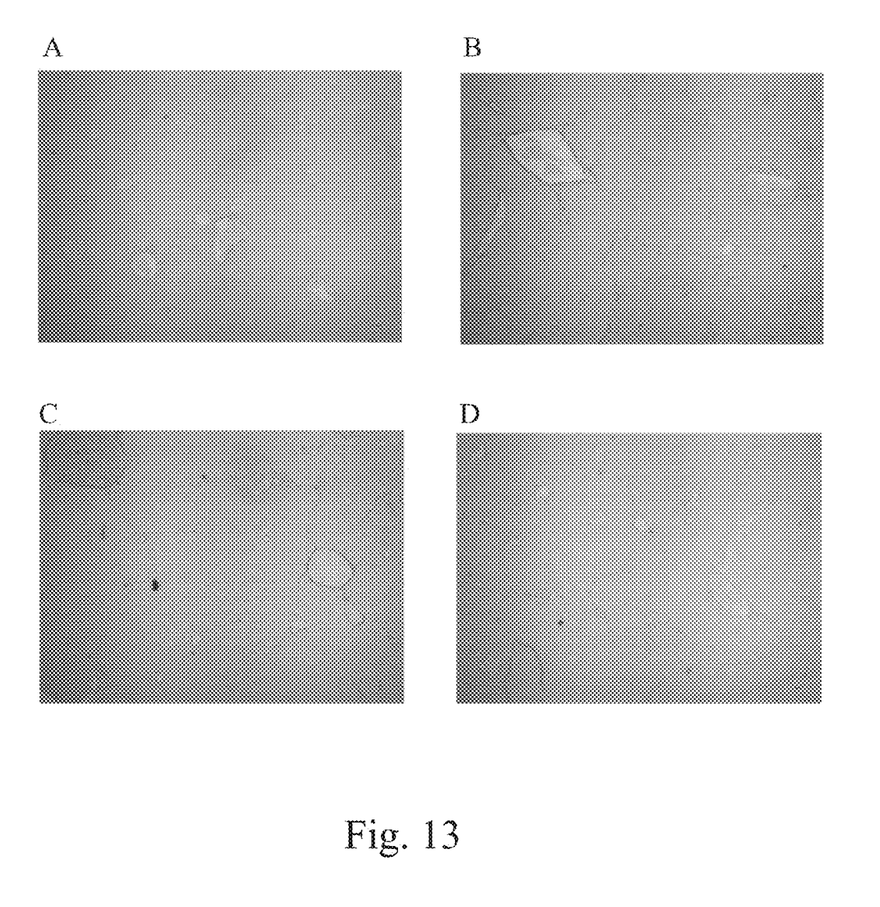

Based on the amount of hydroxyproline in liver is the important diagnosis indicator of fibrosis, the hepatic hydroxyproline of the mice in each group established in example 8 were measured in this example. Moreover, the livers of the mice in each group were collected for histological sections that were followed by H&E staining and sirius red staining for collagen. The results of hydroxyproline measurement, H&E staining and sirius red staining are shown in FIG. 11 to FIG. 13, respectively. Herein, FIG. 11 shows the measured hydroxyproline amount in the liver of each group; FIG. 12 shows the hepatic histology by H&E staining; and the FIG. 13 shows the hepatic histology by sirius staining. The FIG. 12A and FIG. 13A present the group 1; the FIG. 12B and FIG. 13B present the group 2; the FIG. 12C and FIG. 13C present the group 3; and the FIG. 12D and FIG. 13D present the group 4.

In FIG. 11, the result shows that the hepatic hydroxyproline content in the liver of the group 2 is significantly higher than that of the group 1. Furthermore, the hepatic hydroxyproline content in the liver of the group 3 and the group 4 are significantly less than that of the group 2.

The histology in FIG. 12 and FIG. 13 reveals the obvious fat vacuole and more accumulation of fibrosis tissue in the liver of the group 2. In contrast, the mice administrated with the *Dendrobium* polyphenol in the group 3 and the group 4 reveals less fat vacuole and accumulation of fibrosis. These results suggest that the administration with either high dose or low dose of the *Dendrobium* polyphenol is sufficient to suppress the fibrosis and fatty liver progression.

According to the above examples, the invention provides the *Dendrobium* polyphenol that is extracted from the medical plants, genus *Dendrobium*, has several bioactive functions, in particular suppression of the hepatic disorders, such as fibrosis, hepatic lipid accumulation and hepatitis. Furthermore, the *Dendrobium* polyphenol present in the invention is also capable of regulating the blood sugar and slimming.

The polyphenol *Dendrobium* is capable of applying to the pharmaceutical composition for management of hepatic diseases, obesity or diabetes. In addition, it is capable of applying to dietary usage that is sufficient for hepatoprotection and blood sugar regulation.

As the medical composition, the *Dendrobium* polyphenol present in this invention could be manufactured within the currently acceptable pharmaceutical vector or vehicle. It could be manufactured as particle, pastille, powder, liquid, colloid and spraying agent with any delivery way such as oral administration or injection to achieve claimed functions in this invention. In addition, the *Dendrobium* polyphenol could be applied to be the dietary composition within the food such as drinks, tablets, cookies, candies or others for achieving the claimed functions in this invention.

The above-mentioned specification is only for detailedly describing the examples of the invention and shall not be construed as a limitation of the scope of the invention Thus, any modification or change without departing from the characteristics of the invention or any equivalent thereof shall be included in the scope of the invention defined in the following claims.

The invention claimed is:

1. A method for treating obesity, comprising administering to a subject a therapeutically effective amount of *Dendrobium* polyphenol.

2. The method of claim 1, wherein the *Dendrobium* polyphenol is extracted from the plants of the genus *Dendrobium*.

3. The method of claim 2, wherein the plant of genus *Dendrobium* is *Dendrobium tosaense*.

\* \* \* \* \*